United States Patent
Hasson et al.

(10) Patent No.: US 7,593,560 B2
(45) Date of Patent: Sep. 22, 2009

(54) SYSTEMS AND METHODS FOR MONITORING THE AMPLIFICATION AND DISSOCIATION BEHAVIOR OF DNA MOLECULES

(75) Inventors: Kenton C. Hasson, Gaithersburg, MD (US); Gregory A. Dale, Gaithersburg, MD (US); John P. Keady, Fairfax Station, VA (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 0 days.

(21) Appl. No.: 11/947,237

(22) Filed: Nov. 29, 2007

(65) Prior Publication Data

US 2008/0130971 A1    Jun. 5, 2008

Related U.S. Application Data

(60) Provisional application No. 60/861,712, filed on Nov. 30, 2006.

(51) Int. Cl.
*G06K 9/00* (2006.01)
(52) U.S. Cl. .................................. 382/129
(58) Field of Classification Search ............ None
See application file for complete search history.

(56) References Cited

U.S. PATENT DOCUMENTS

| | | | |
|---|---|---|---|
| 4,589,140 A * | 5/1986 | Bishop et al. | 382/148 |
| 4,642,813 A * | 2/1987 | Wilder | 382/147 |
| 4,984,075 A * | 1/1991 | Munaoka | 348/26 |
| 5,717,780 A * | 2/1998 | Mitsumune et al. | 382/141 |
| 6,271,022 B1 | 8/2001 | Bochner | |
| 6,689,565 B2 | 2/2004 | Nikiforov | |
| 6,713,264 B2 | 3/2004 | Luttermann et al. | |
| 6,960,437 B2 | 11/2005 | Enzelberger et al. | |
| 6,979,567 B2 | 12/2005 | Herron et al. | |
| 7,081,954 B2 | 7/2006 | Sandstrom | |
| 7,090,133 B2 | 8/2006 | Zhu | |
| 2001/0036231 A1 | 11/2001 | Easwar et al. | |
| 2001/0048483 A1 * | 12/2001 | Steinberg et al. | 348/587 |
| 2002/0160405 A1 * | 10/2002 | Ramsey et al. | 435/6 |
| 2005/0042639 A1 | 2/2005 | Knapp et al. | |
| 2005/0117049 A1 | 6/2005 | Suzuki | |

(Continued)

FOREIGN PATENT DOCUMENTS

WO    2005075683 A1    8/2005

OTHER PUBLICATIONS

Lagally et al., "Single Molecule DNA Amplification and Analysis in an Integrated Microfluidic Device," Anal. Chem., 73:565-570 (2001).
Kopp et al., "Chemical Amplification: Continuous Flow PCR on a Chip," Science, 280:1046-1048 (1998).
Park et al., "Cylindrical Compact Thermal-Cycling Device for Continuous-Flow Polymerase Chain Reaction," Anal. Chem., 75:6029-6033 (2003).

*Primary Examiner*—Matthew C Bella
*Assistant Examiner*—Alex Liew
(74) *Attorney, Agent, or Firm*—Rothwell, Figg, Ernst & Manbeck PC

(57) ABSTRACT

The present invention relates to systems and methods for monitoring the amplification of DNA molecules and the dissociation behavior of the DNA molecules.

12 Claims, 12 Drawing Sheets

U.S. PATENT DOCUMENTS

| | | |
|---|---|---|
| 2005/0135655 A1 | 6/2005 | Kopf-Sill et al. |
| 2005/0189224 A1 | 9/2005 | Parce |
| 2005/0231723 A1 | 10/2005 | Blasenheim et al. |
| 2005/0266448 A1 | 12/2005 | Hagiwara et al. |
| 2006/0000722 A1 | 1/2006 | Parce et al. |
| 2006/0006067 A1 | 1/2006 | Unger |
| 2007/0026421 A1 | 2/2007 | Sundberg et al. |

* cited by examiner

SYSTEMS AND METHODS FOR MONITORING THE AMPLIFICATION AND DISSOCIATION BEHAVIOR OF DNA MOLECULES

This application claims the benefit of Provisional Patent Application Ser. No. 60/861,712, filed on Nov. 30, 2006, which is incorporated herein by reference.

BACKGROUND

1. Field of the invention

The present invention relates to systems and methods for monitoring the amplification of DNA molecules and the dissociation behavior of the DNA molecules.

2. Discussion of the Background

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, correct identification of crime scene features, the ability to propagate industrial organisms and many other techniques. Determination of the integrity of a nucleic acid of interest can be relevant to the pathology of an infection or cancer. One of the most powerful and basic technologies to detect small quantities of nucleic acids is to replicate some or all of a nucleic acid sequence many times, and then analyze the amplification products. Polymerase chain reaction (PCR) is a well-known technique for amplifying DNA.

With PCR, one can quickly produce millions of copies of DNA starting from a single template DNA molecule. PCR includes a three phase temperature cycle of denaturation of the DNA into single strands, annealing of primers to the denatured strands, and extension of the primers by a thermostable DNA polymerase enzyme. This cycle is repeated a number of times so that at the end of the process there are enough copies to be detected and analyzed. For general details concerning PCR, see Sambrook and Russell, *Molecular Cloning—A Laboratory Manual* (3rd Ed.), Vols. 1-3, Cold Spring Harbor Laboratory, Cold Spring Harbor, N.Y. (2000); *Current Protocols in Molecular Biology*, F. M. Ausubel et al., eds., Current Protocols, a joint venture between Greene Publishing Associates, Inc. and John Wiley & Sons, Inc., (supplemented through 2005) and *PCR Protocols A Guide to Methods and Applications*, M. A. Innis et al., eds., Academic Press Inc. San Diego, Calif. (1990).

In some applications, it is important to monitor the accumulation of DNA products as the amplification process progresses. Real-time PCR refers to a growing set of techniques in which one measures the buildup of amplified DNA products as the reaction progresses, typically once per PCR cycle. Monitoring the amplification process over time allows one to determine the efficiency of the process, as well as estimate the initial concentration of DNA template molecules. For general details concerning real-time PCR see *Real-Time PCR: An Essential Guide*, K. Edwards et al., eds., Horizon Bioscience, Norwich, U.K. (2004).

More recently, a number of high throughput approaches to performing PCR and other amplification reactions have been developed, e.g., involving amplification reactions in microfluidic devices, as well as methods for detecting and analyzing amplified nucleic acids in or on the devices. Thermal cycling of the sample for amplification is usually accomplished in one of two methods. In the first method, the sample solution is loaded into the device and the temperature is cycled in time, much like a conventional PCR instrument. In the second method, the sample solution is pumped continuously through spatially varying temperature zones. See, for example, Lagally et al. (*Anal Chem* 73:565-570 (2001)), Kopp et al. (*Science* 280:1046-1048 (1998)), Park et al. (*Anal Chem* 75:6029-6033 (2003)), Hahn et al. (WO 2005/075683), Enzelberger et al. (U.S. Pat. No. 6,960,437) and Knapp et al. (U.S. Patent Application Publication No. 2005/0042639).

Once there are a sufficient number of copies of the original DNA molecule, the DNA can be characterized. One method of characterizing the DNA is to examine the DNA's dissociation behavior as the DNA transitions from double stranded DNA (dsDNA) to single stranded DNA (ssDNA) with increasing temperature. The process of causing DNA to transition from dsDNA to ssDNA is sometimes referred to as a "high-resolution temperature (thermal) melt (HRTm)" process, or simply a "high-resolution melt" process.

Accordingly, what is desired is a system for monitoring the DNA amplification process and for determining the DNA's dissociation behavior.

SUMMARY OF THE INVENTION

The present invention relates to systems and methods for performing and monitoring real-time PCR and HRTm analysis.

In one aspect, the present invention provides a method that includes the steps of: introducing a sample of a solution comprising nucleic acid into a microchannel; forcing the sample to move though the channel; defining a first window of a pixel array of an image sensor; defining a second window of the pixel array, wherein the center of the second window is spaced apart from the center of the first window; and while the sample is moving through the microchannel, performing the steps of: (a) exposing the first window of the pixel array to light emitted from the sample at a time when the sample is within a field of view of first window and then selectively outputting first image data from the pixel array, wherein the step of selectively outputting the first image data from the pixel array comprises outputting data from only the first window of the pixel array; and (b) after performing step (a), exposing the second window of the pixel array to light emitted from the sample at a time when the sample is within a field of view of second window and then selectively outputting second image data from the pixel array, wherein the step of selectively outputting the second image data from the pixel array comprises outputting data from only the second window of the pixel array. The step of defining the second window may occur after step (a).

In some embodiments, when the step of exposing the first window of the pixel array to light emitted from the sample is performed, the center of the first window corresponds substantially to the center of the sample, and when the step of exposing the second window of the pixel array to light emitted from the sample is performed, the center of the second window corresponds substantially to the center of the sample.

In some embodiments the size of the second window may be less than or greater than the size of the first window, and the step of defining the second window includes processing the first image data to determine whether the amount of light received at a pixel located at an edge of the first window exceeds or equals a predetermined threshold.

In some embodiments, the method may also include the steps of: receiving from a first sensor a first signal indicating that the sample has been detected by the first sensor and receiving from a second sensor a second signal indicating that the sample has been detected by the second sensor, wherein the first sensor is positioned to detect when the sample enters the field of view of the image sensor and the second sensor is positioned to detect when the sample leaves the field of view of the image sensor.

In some embodiments, the step of defining the first window of the pixel array comprises determining the size of the window, wherein the determination is based, at least in part, on the length of the sample, and the step of defining the second window of the pixel array comprises determining the location of the center of the second window, wherein the determination is based, at least in part, on a speed at which the sample moves through the channel.

In another aspect, the present invention provides a system that includes the following elements: a chip comprising a microchannel for receiving a sample of solution comprising nucleic acid and for providing a path for the sample to traverse; an image sensor having a pixel array, wherein at least a portion of the microchannel is within a field of view of the pixel array; and an image sensor controller configured to: (a) read only a first window of the pixel array at time when the sample is within a field of view of the first window, and (b) read only a second window of the pixel array at time when the sample is within a field of view of the second window, wherein the center of the second window is spaced apart from the center of the first window.

In another aspect, the present invention provides a method that includes the following steps: introducing a sample of a solution comprising nucleic acid into a channel; causing the sample to move though the channel; defining a first window of a pixel array of an image sensor; defining a second window of the pixel array, wherein the center of the second window is spaced apart from the center of the first window; while the sample is moving through the microchannel, performing the steps of: (a) windowing the image sensor so that image data from the first window is output to a data buffer, wherein said image data comprises data from which the intensity of emissions from the sample can be determined; and (b) after performing step (a), windowing the image sensor so that image data from the second window is output to a data buffer, wherein said image data comprises data from which the intensity of emissions from the sample can be determined.

In yet another aspect, the present invention provides a method that includes the following steps: introducing a first sample of a solution comprising nucleic acid into a first channel; introducing a second sample of a solution comprising nucleic acid into a second channel; causing the first sample to move though the first channel; causing the second sample to move though the second channel; defining a first window of a pixel array of an image sensor, wherein at least a portion of the first channel is within the field of view of the first window; defining a second window of the pixel array, wherein at least a portion of the second channel is within the field of view of the second window and wherein the center of the second window is spaced apart from the center of the first window; while the samples are moving through the respective channels, performing the steps of: (a) windowing the image sensor so that image data from the first window is output to a data buffer, wherein said image data comprises data from which the intensity of emissions from the first sample can be determined; and (b) after performing step (a), windowing the image sensor so that image data from the second window is output to a data buffer, wherein said image data comprises data from which the intensity of emissions from the second sample can be determined.

The above and other embodiments of the present invention are described below with reference to the accompanying drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements. Additionally, the left-most digit(s) of a reference number identifies the drawing in which the reference number first appears.

DETAILED DESCRIPTION OF PREFERRED EMBODIMENTS

Figure 1:
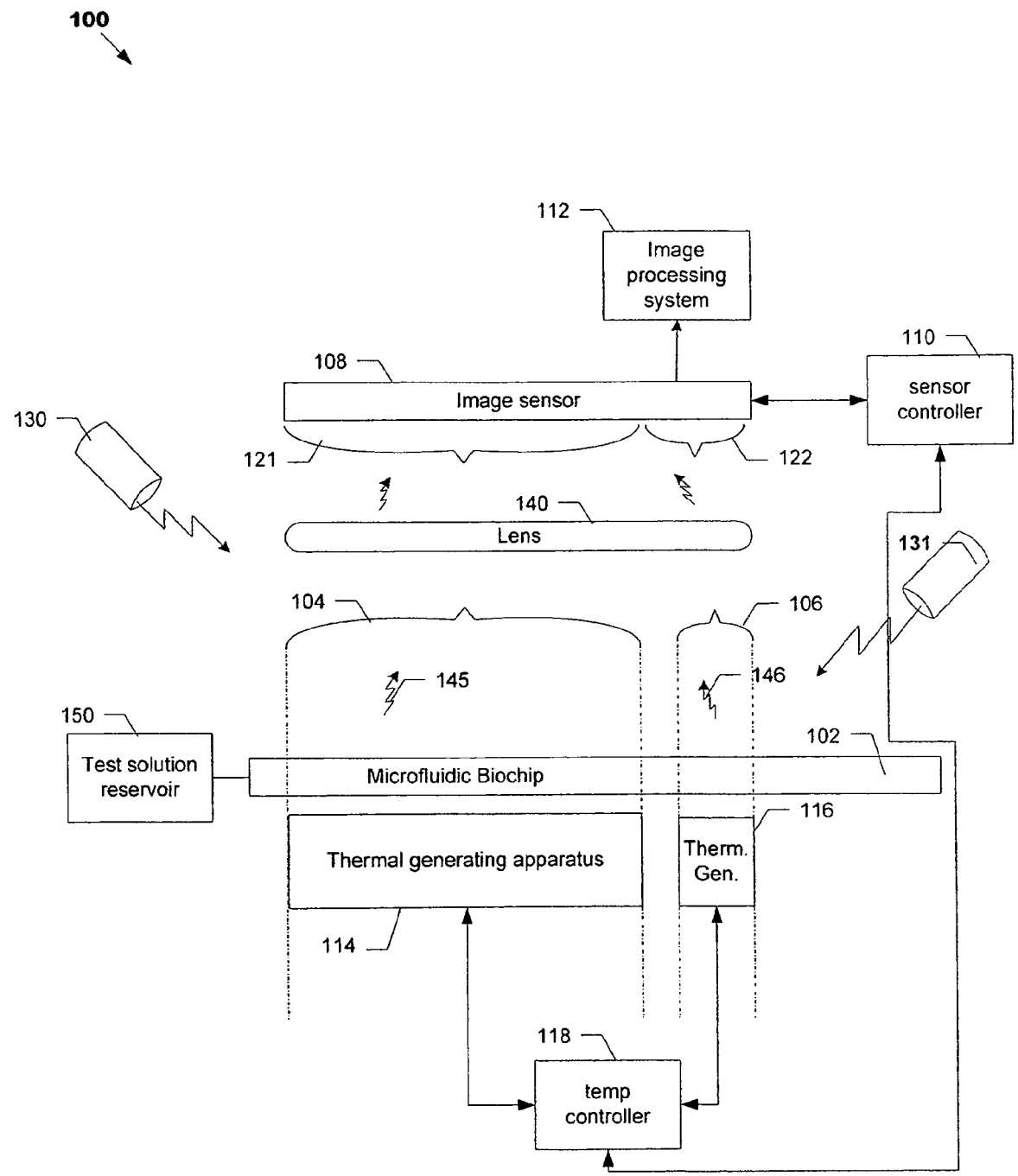
FIG. 1 illustrates a nucleic acid analysis system 100 according to an embodiment.
Figure 2:
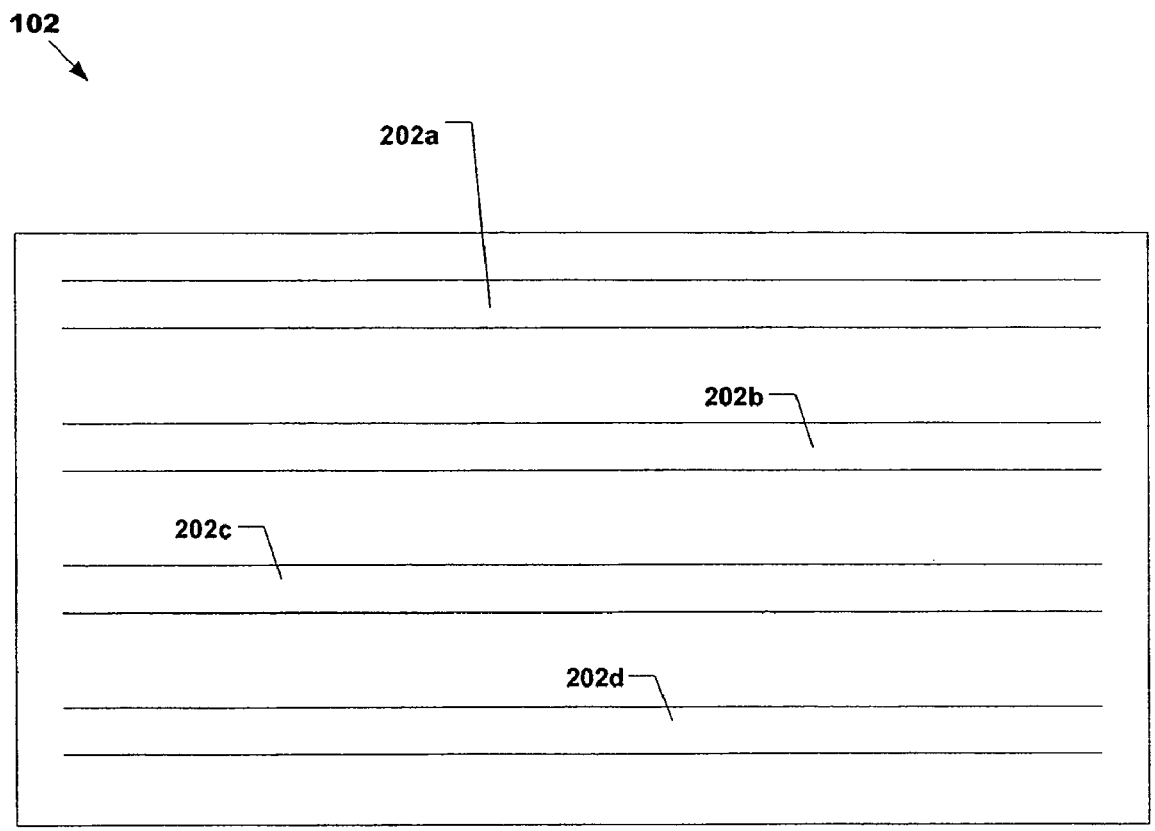
FIG. 2 is a top view of biochip 102 according to some embodiments.

Referring to the drawings, FIG. 1 illustrates a nucleic acid analysis system 100 according to an embodiment. As shown in FIG. 1, system 100 includes a microfluidic biochip 102. FIG. 2 is a top view of biochip 102 according to some embodiments. As shown in FIG. 2, biochip 102 includes a number of microfluidic channels 202. In the example shown, there are 4 microfluidic channels (i.e., channels 202a,b,c,d), but it is contemplated that chip 102 may have more or less than 4 channels.

In some embodiments, when system 100 is in use, at least one channel 202 receives a sample (or "bolus") of a solution containing real-time PCR reagents. A force may be used to cause the bolus to travel through the channel 202 and a thermal generating apparatus 114 may be used to cycle the temperature of the bolus as described above while the bolus moves through the channel 202. One system and method for performing PCR in a microfluidic device is disclosed in U.S. patent application Ser. No. 11/505,358, filed on Aug. 17, 2006, incorporated herein by reference.

As further shown in FIG. 1, analysis system 100 may further include an image sensor 108, a controller 110 configured to control image sensor 108, and an image processing system 112 configured to process the image data produced by image sensor 108. Image sensor 108 may be implemented using a CMOS image sensor, a CCD image sensor, or other image sensor. For example, in one embodiment, sensor 108 is a CMOS sensor with an effective 12.7 mega pixel resolution and having a size of 36×24 mm, which is available from Canon Inc.

Figure 3:
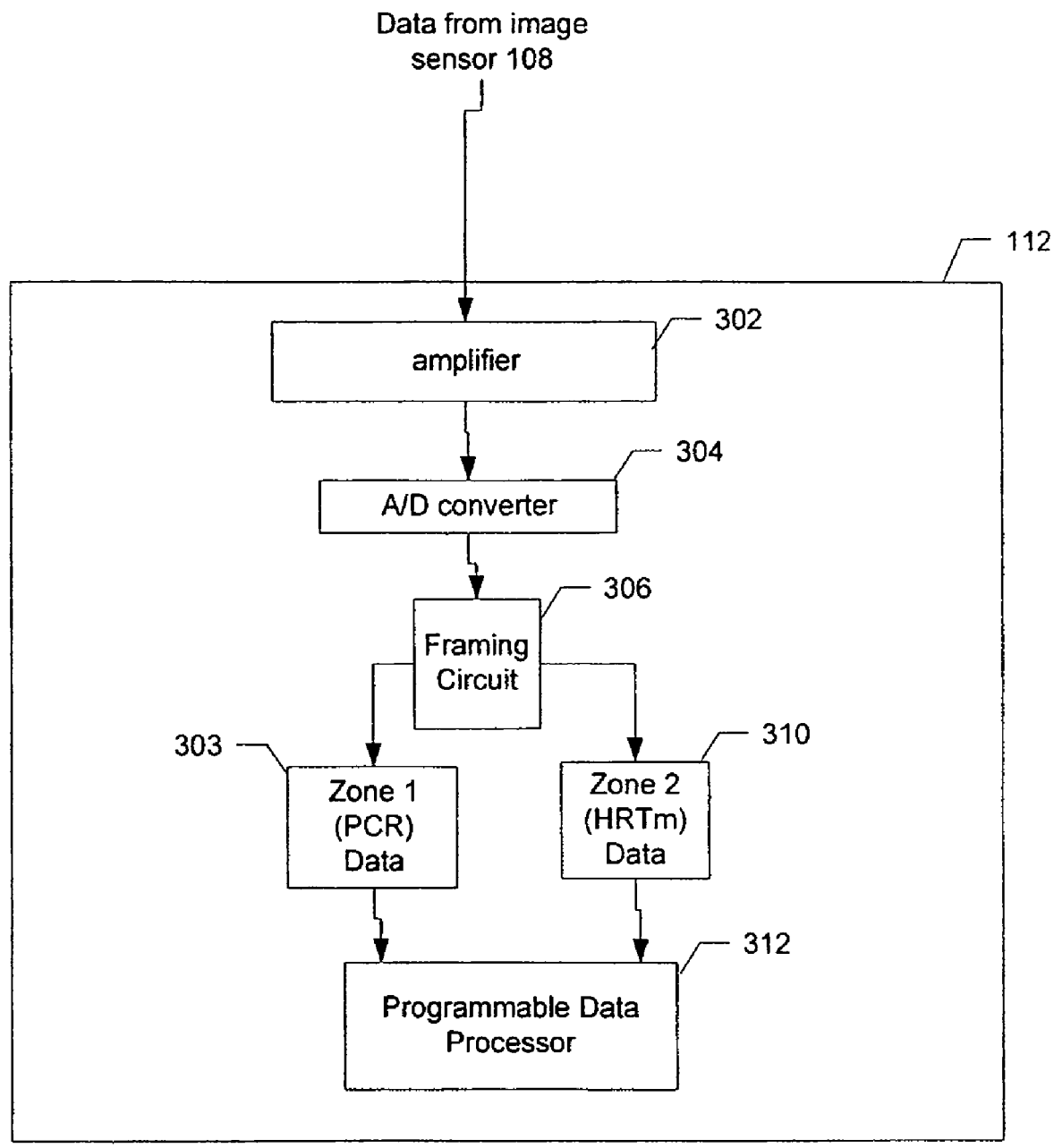
FIG. 3 is a functional block diagram illustrating an embodiment of image processing system 112.

Referring now to FIG. 3, FIG. 3 is a functional block diagram illustrating an embodiment of image processing system 112. As shown in FIG. 3, system 112 receives data output from image sensor 108. System 112 may include an amplifier 302 to amplify the data from image sensor 108. In one non-limiting embodiment, amplifier 302 may amplify the data for greater sensitivity. The amplified data may be converted to a digital signal by, for example, a 16 bit analog-to-digital (A/D) converter 304. In one embodiment, utilization of a 16 bit A/D converter provides a high level of dynamic range and low end bit resolution. The digital signal output from A/D converter 304 may be processed by a framing circuit 306, which may be configured to store data produced during an HRTm process in a zone 1 data buffer 308 and store data produced during a PCR process in a zone 2 data buffer 310. A programmable data processor 312 may be programmed to process data in buffers 310 and 312 to, among other things, determine and record the intensity of the fluorescence from samples that undergo the PCR and HRTm processing.

Figure 4:
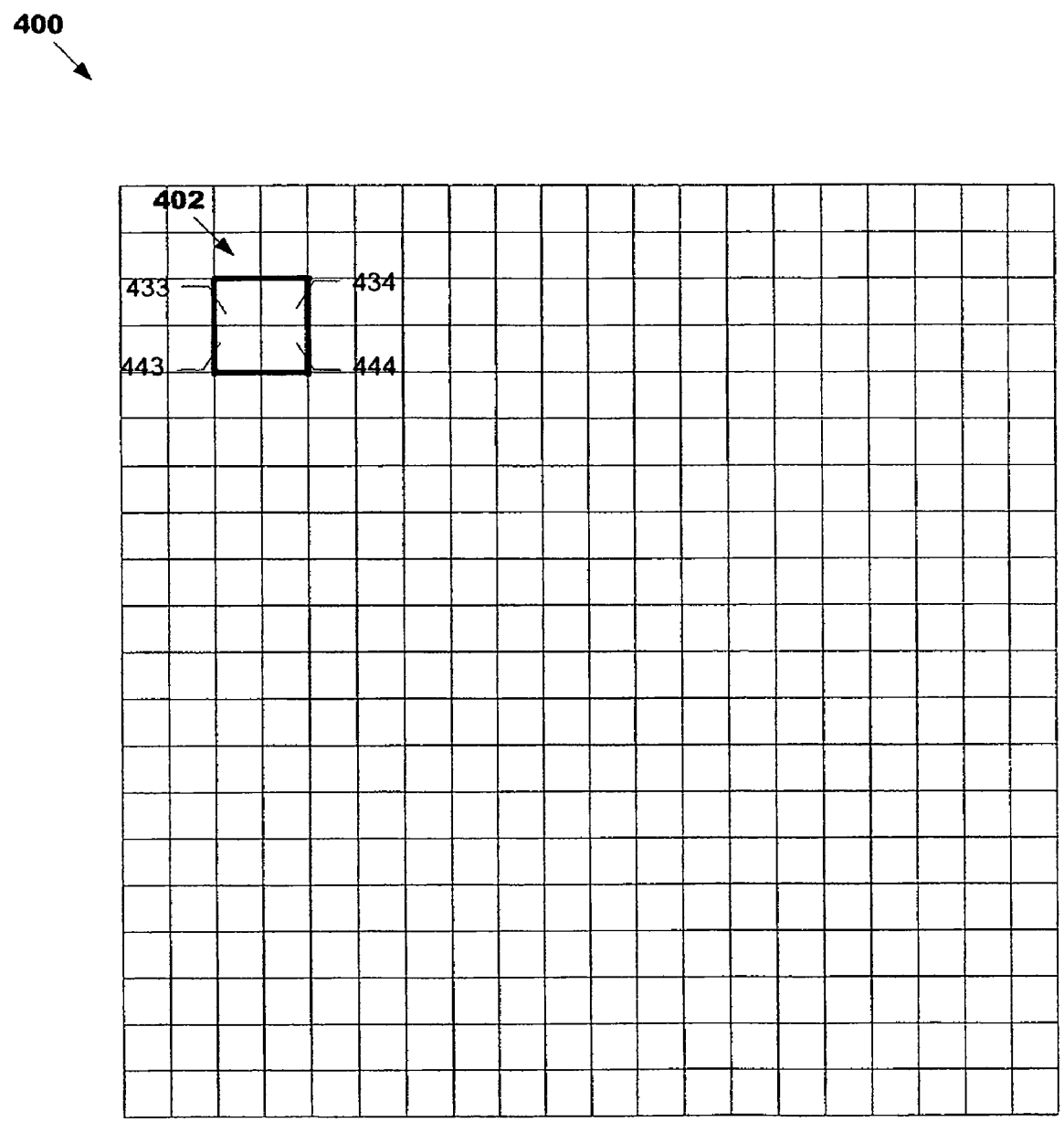
FIG. 4 shows an exemplary pixel array 400.

As is well known in the art of imaging, image sensor 108 may have an array of pixels. Referring now to FIG. 4, FIG. 4 shows an exemplary pixel array 400. For the sake of clarity, pixel array 400 includes only 400 pixels. However, it is well understood that the pixel array of image sensor 108 may have over 1 million pixels. In at least one embodiment, image sensor 108, lens 140 and chip 102 are arranged so that at least a significant portion of each channel of chip 102 is within the field of view of the pixel array 400 of image sensor 108. Also, in at least one exemplary embodiment the image sensor 108 has the ability to read out a predefined portion or "window" of the pixel array (this is known as windowing). FIG. 4 shows an example window 402, which consists of pixels 433, 434, 443 and 444. As is well known in the art, image sensor 108 may have the ability to read out only the pixels that make up window 402 (i.e., to obtain image data from only those pixels within window 402). For example, image sensor 108 may have pixel-row and pixel-column select circuits that enable one to read out only a particular window. Embodiments of the present invention can make use of this feature as described below.

Figure 5:
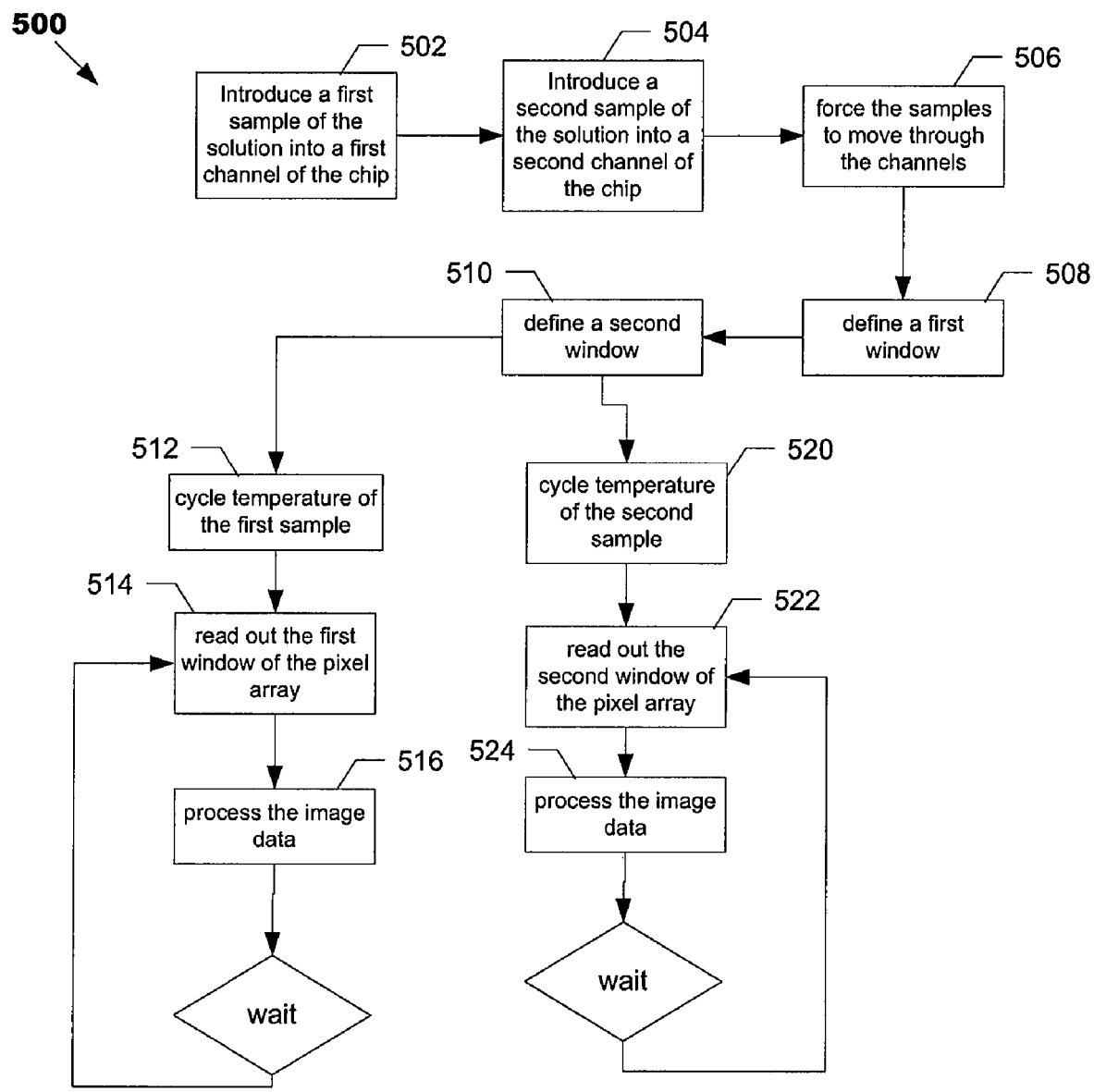
FIG. 5 illustrates a process according to an embodiment.
Figure 6:
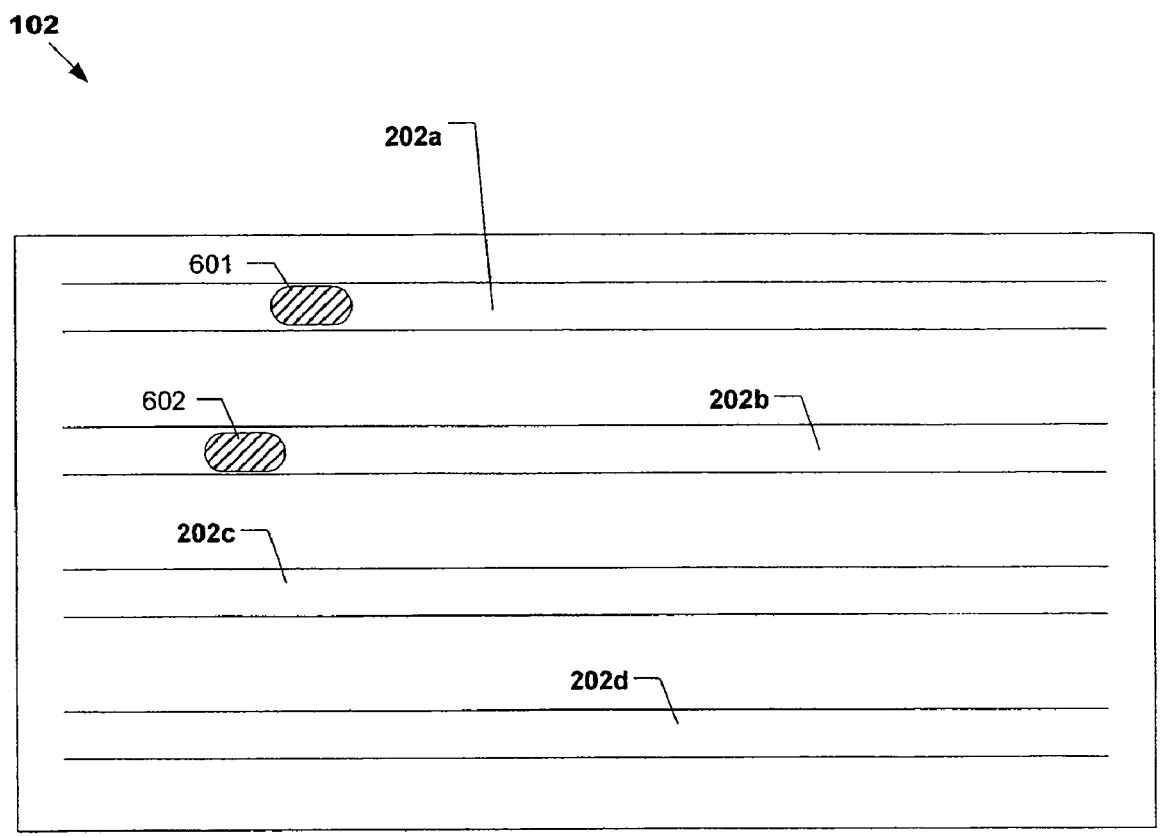
FIG. 6 pictorially illustrates some of the steps of the process shown in FIG. 5.

Referring now to FIG. 5, FIG. 5 is a flow chart illustrating a process 500 according to an embodiment of the invention. Process 500 may begin in step 502, where a first sample of a solution comprising nucleic acid is introduced into a channel of chip 102 (for the sake of discussion we will assume the sample is introduced into channel 202a). In step 504, a second sample of a solution comprising nucleic acid is introduced into another channel 202 of chip 102 (for the sake of discussion we will assume the sample is introduced into channel 202b). Steps 502 and 504 are illustrated in FIG. 6, which shows the first sample (i.e., sample 601) in channel 202a and shows the second sample (i.e., sample 602 in channel 202b). In step 506, a pressure force is applied to samples 601 and 602 causing them to move through channels 202a,b, respectively.

Figure 7:
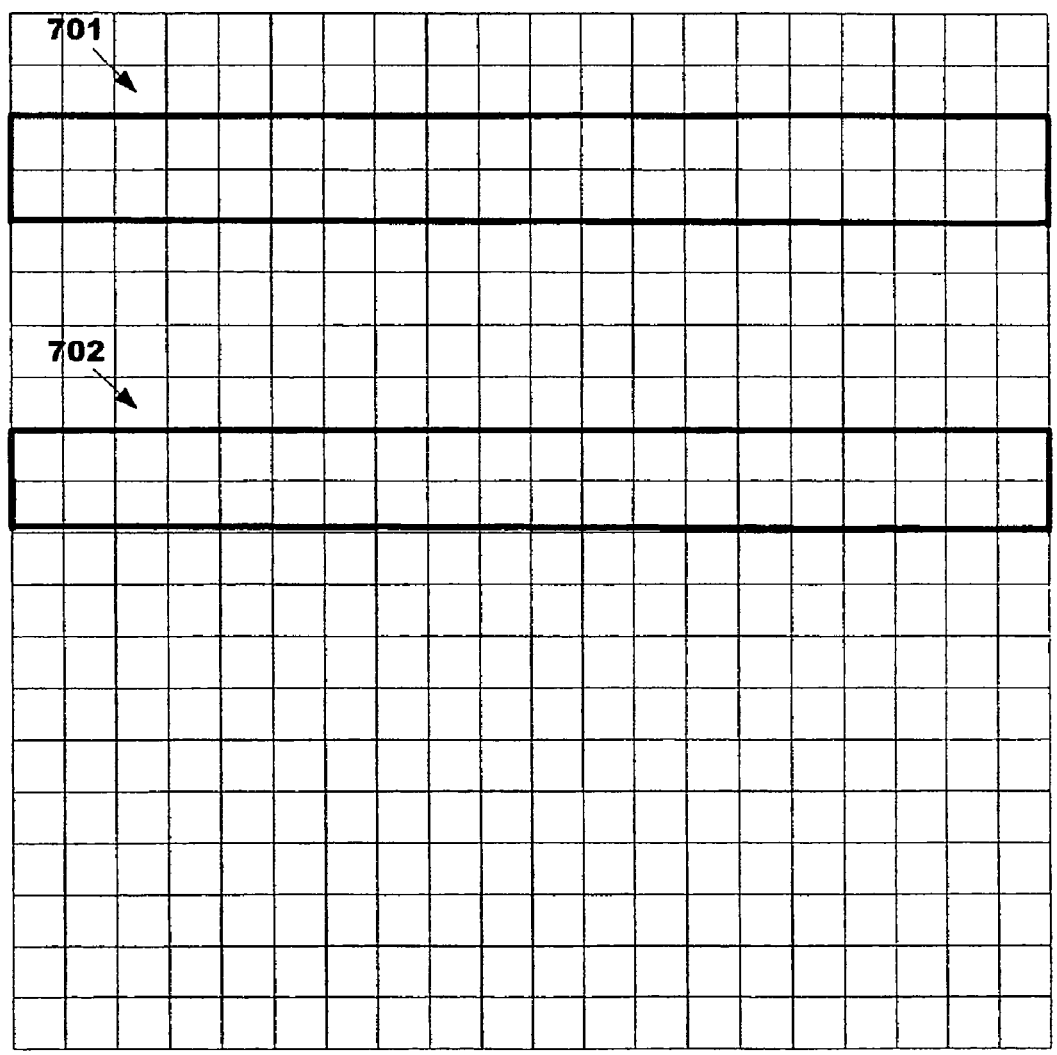
FIG. 7 shows a first window of a pixel array and a second window of the pixel array.

In step 508, a first window of pixel array 400 is defined such that at least a portion of channel 202a is within the field of view of the first window. In step 510, a second window of pixel array 400 is defined such that at least a portion of channel 202b is within the field of view of the second window and such that the center of the second window is spaced apart from the center of the first window. Steps 508 and 510 are illustrated in FIG. 7, which shows a first window 701 of pixel array 400 and a second window 702 of pixel array 400.

While sample 601 moves through the field of view of window 701, step 512 may be performed. Similarly, while sample 601 moves through the field of view of window 701, step 520 may be performed. In step 512 the temperature of sample 601 is cycled a number of times to achieve amplification of the nucleic acid present within sample 601 and in step 520 the temperature of sample 602 is cycled to achieve amplification of the nucleic acid present within sample 602.

Figure 8:
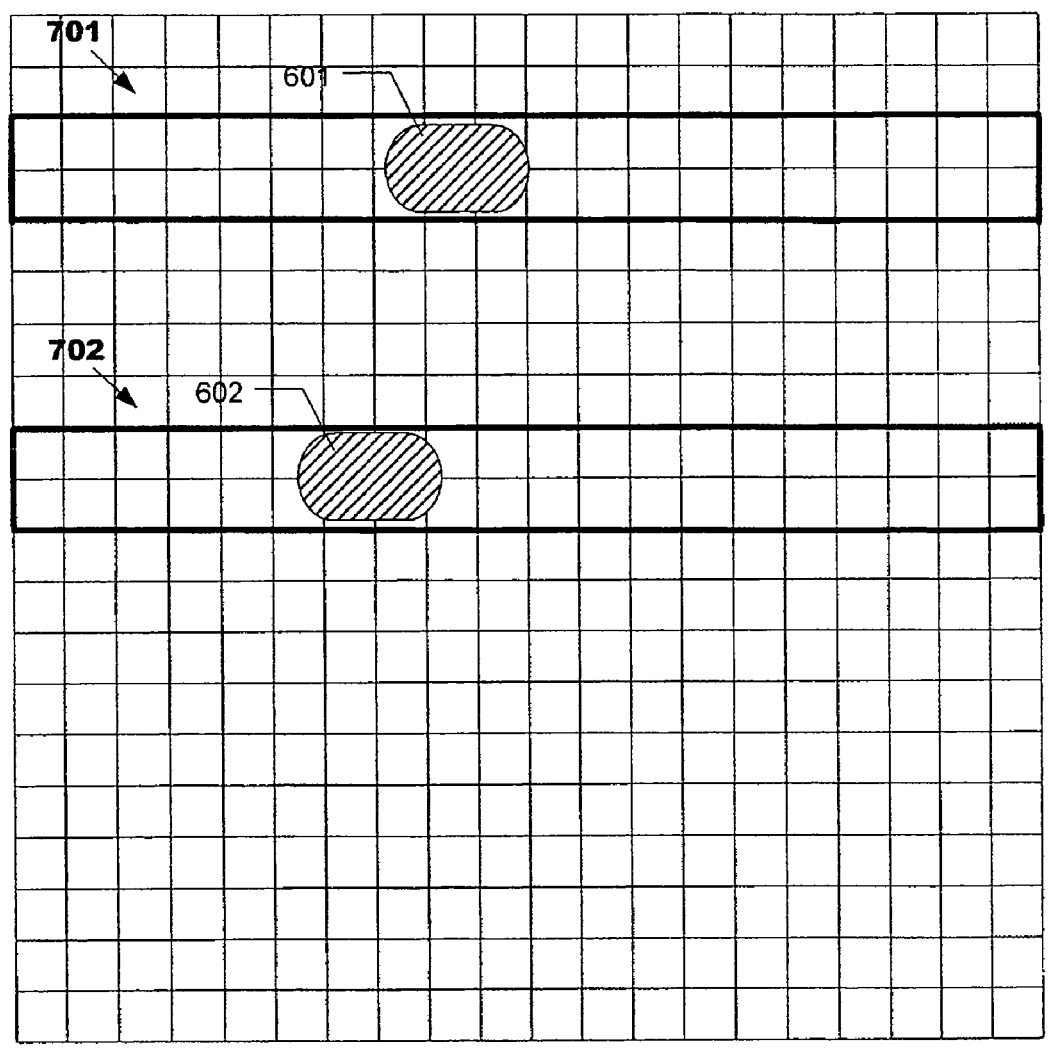
FIG. 8 pictorially illustrates some of the steps of the process shown in FIG. 5.

While steps 512 and 520 are being performed, steps 514 and 522 are performed. In step 514, controller 110 windows image sensor 108 so that image data from window 701 is output to a data buffer and in step 516 the image data is processed by image processing system 112. This image data comprises data from which the intensity of emissions from sample 601 can be determined because when step 514 is performed, sample 601 is within the field of view of window 701, as illustrated in FIG. 8. Similarly, in step 522, controller 110 windows image sensor 108 so that image data from window 702 is output to a data buffer and in step 524 the image data is processed by image processing system 112. This image data comprises data from which the intensity of emissions from sample 602 can be determined because when step 522 is performed, sample 602 is within the field of view of window 702, as illustrated in FIG. 8. As shown in FIG. 8, the width of windows 701 and 702 may be configured to be slightly greater than the width of the respective channels (e.g., the width of window 701 may be equal to the pixel width of channel 202a plus not more than several pixels).

As illustrated in FIG. 5, steps 514, 516, 522 and 524 may be repeated.

In some embodiments, prior to performing steps 514 and 522 again, windows 701 and 702 may be redefined. For example, windows 701 and/or 702 may be made smaller so that less image data is transferred to the data buffers on subsequent performance of step 514 and/or 522. In some embodiments, the window may be redefined so that the size of the window is equal to the pixel size of the sample plus a few pixels, and the center of the window corresponds substantially to the location of the center of the sample.

Figure 9:
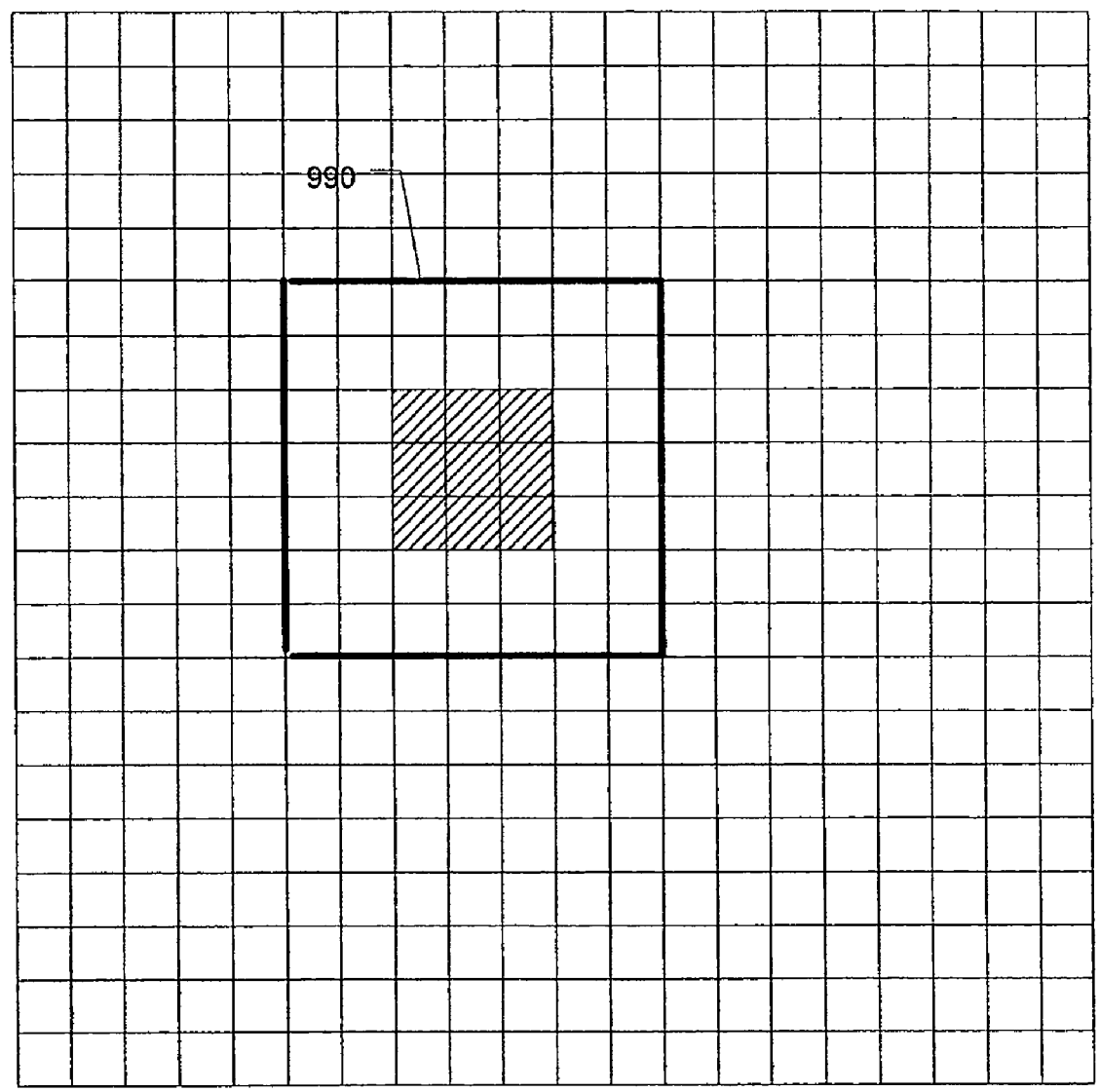
FIG. 9 pictorially illustrates a process according to an embodiment.

To determine the pixel size of the sample, image processing system 112 may be programmed to determine the pixels of pixel array that received at least a predetermined threshold of light from the sample. The window may then be defined to include those pixels plus, for each pixel, not more than a predetermined number of neighboring pixels (e.g., not more than about 5 neighboring pixels). This process is illustrated in FIG. 9. As shown in FIG. 9, the shaded pixels represent the pixels that received at least a predetermined amount of light from the sample during a predetermined integration period. Given this information, a window can be defined to include not only these pixels, but also neighboring pixels for each pixel. Such a window 990 is shown in FIG. 9. As illustrated, window 990 includes not only not only the pixels that received at least the predetermined amount of light, but also two neighboring pixels for each said pixel.

In one embodiment, to determine the point of the pixel array 400 that corresponds to the location of the center of the sample 601 at some specific point in time, processing system 112 may compute the location based on knowledge of the location of the center of the sample 601 at some previous point in time (e.g., the point in time when step 514 was last performed), the average velocity of the sample during the time period between the specific point in time and the previous point in time, and the time difference between the specific point in time and the previous point in time. The location of the center of the sample 601 at some previous point in time and the average velocity of the sample may be known or may be derived from image data captured by image sensor 108. This process is illustrated in FIG. 10.

Figure 10:
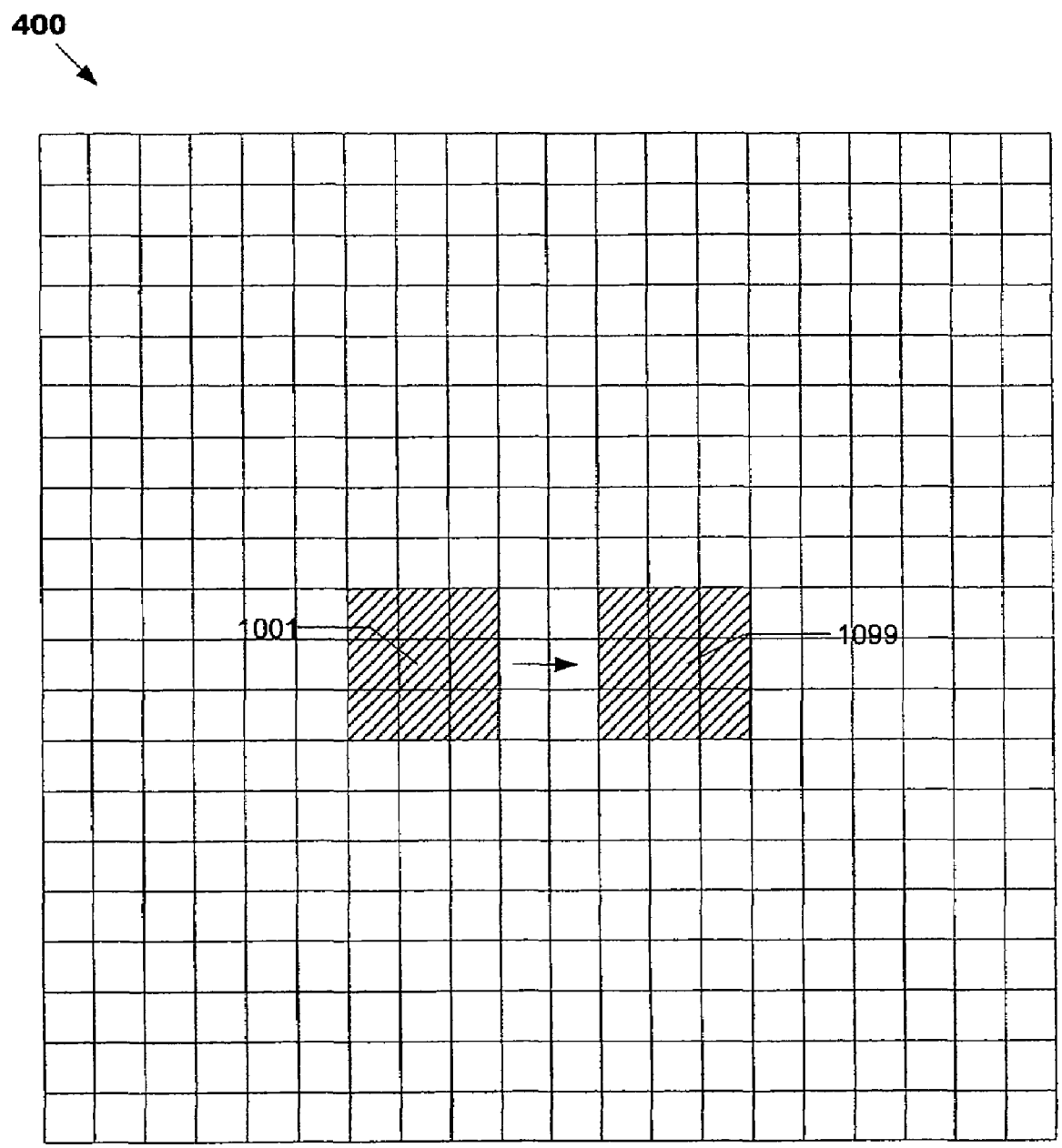
FIG. 10 pictorially illustrates a process according to an embodiment.

FIG. 10 shows a first group of pixels that received at least a predetermined amount of light from the sample at time t1. Pixel 1001 is in the center of this group of pixels. With this information, the point of pixel array 400 that corresponds to the location of the center of the sample at time t2 can be determined using the following formula: S*(t2−t1), where s is the speed of the sample as it moves through the channel in units of pixels/unit of time. For example if t2−t1 equals 1 second and s equals 5 pixels per second and one knows the sample moves in the direction of arrow 1090, then one can determine that at time t2 the center of the sample will be at pixel 1099.

Figure 11:
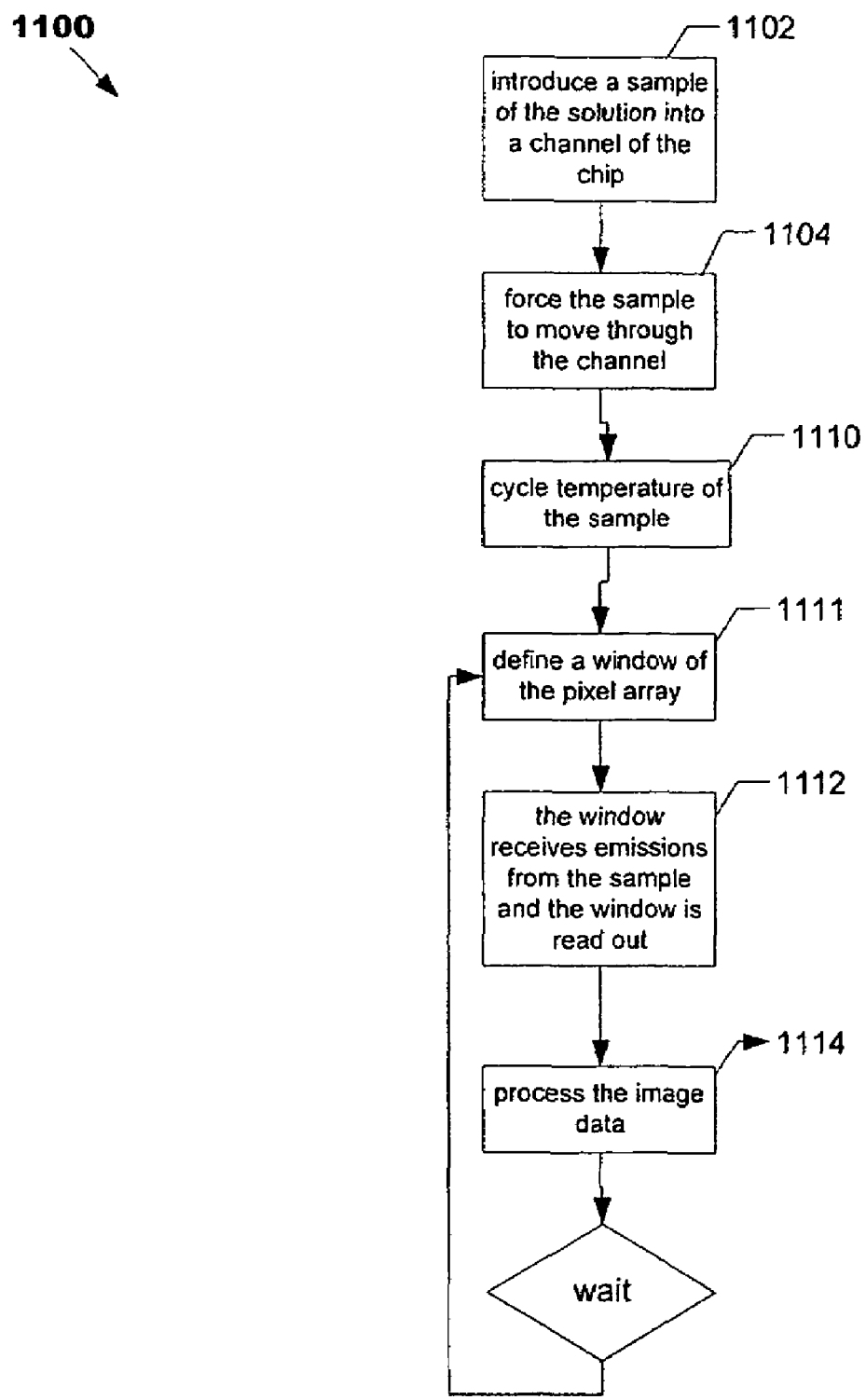
FIG. 11 is a flow chart illustrating a process according to another embodiment.

Referring now to FIG. 11, FIG. 11 is a flow chart illustrating a process 1100 according to an embodiment of the invention. Process 1100 may begin in step 1102, where a sample of a solution comprising nucleic acid is introduced into a channel of chip 102. In step 1104, a force is applied to the sample causing it to move through the channel.

While the sample is within at least some portion of the channel, step 1110 is performed. In step 1110 the temperature of the sample is cycled a number of times to achieve amplification of the nucleic acid present within sample.

While step 1110 is being performed, the following steps are performed. In step 1111 a window of pixel array 400 is defined such that at some particular point in time the sample will be in the field of view of the window. Preferably, the window is sized and positioned such that the window is substantially equal to the pixel size of the sample (e.g., the pixel size of the sample plus a few pixels), and such that at the particular point in time the center of the window corresponds substantially to the location of the center of the sample. When the particular point in time occurs, step 1112 is performed. In step 1112, the window receives emissions from the sample and then controller 110 windows image sensor 108 so that image data from the window is output to a data buffer. Preferably, in step 1112 image sensor 108 is windowed such that only the image data from the window is output to the data buffer. This image data comprises data from which the intensity of emissions from the sample can be determined. In step 1114, the image data may be processed by image processing system 112.

As illustrated in FIG. 11, steps 1111 and 1112 may be repeated.

Figure 12:
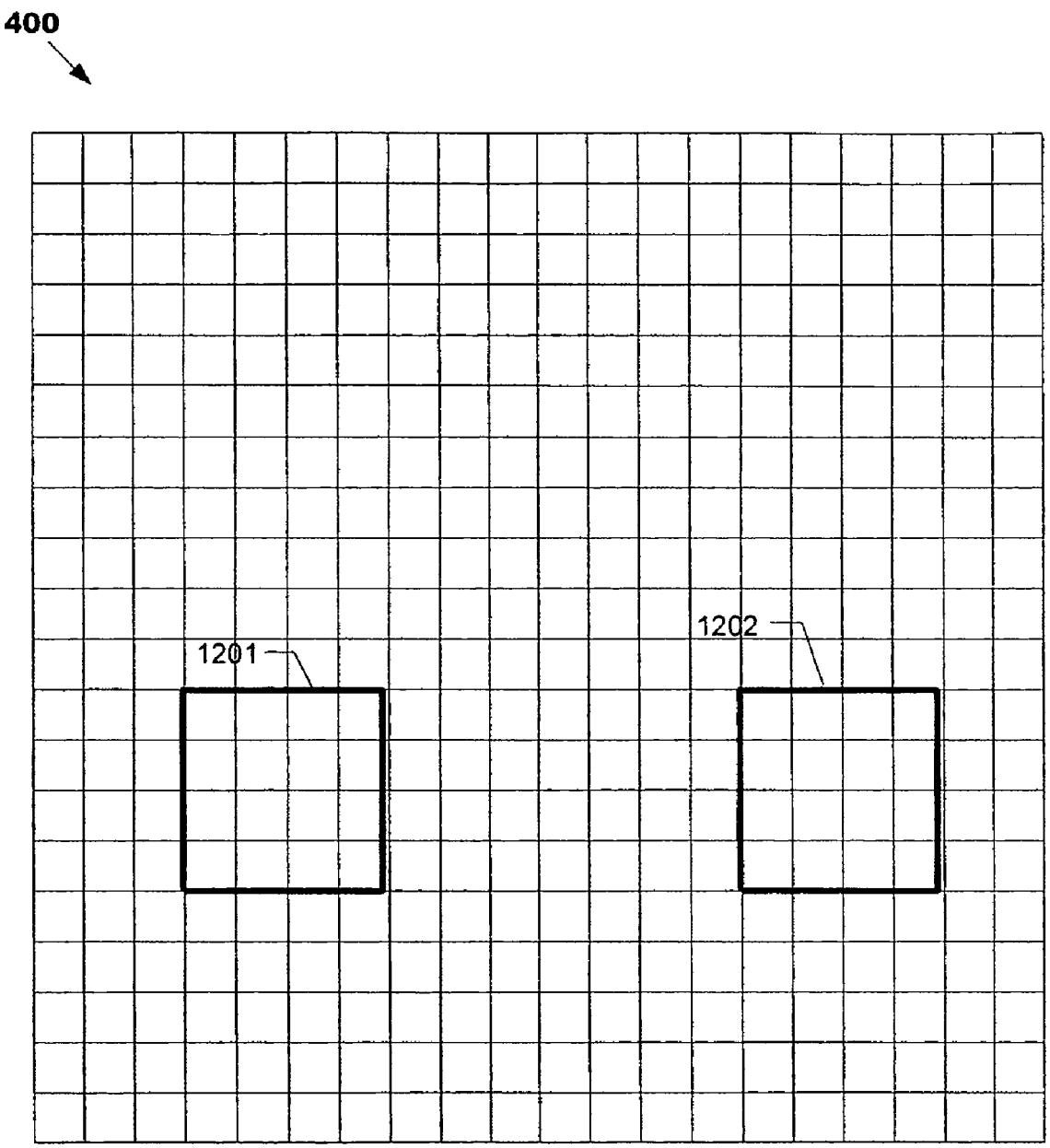
FIG. 12 pictorially illustrates some of the steps of the process shown in FIG. 11.

Process 1100 is pictorially illustrated in FIG. 12, which shows a first window 1201 of pixel array 400 and a second window 1202 of pixel array 400. Window 1201 is defined the first time step 1111 is performed and window 1202 is defined the second time step 1111 is performed. As shown in FIG. 12, a window follows the sample by keeping track of the location of the sample. Thus, by keeping track of the location of the sample, one need not read out the entire pixel array 400 in order to obtain information about a sample, rather one need only read out a small window of the pixel array.

While various embodiments of the present invention have been described above, it should be understood that they have been presented by way of example only, and not limitation. Thus, the breadth and scope of the present invention should not be limited by any of the above-described exemplary embodiments.

Additionally, while the processes described above are shown as a sequence of steps, this was done solely for the sake of illustration. Accordingly, it is contemplated that some steps may be added, some steps may be omitted, and the order of the steps may be re-arranged.

Additional features are disclosed in the document attached hereto as appendix A.

For the claims below the words "a" and "an" should be construed as "one or more."

What is claimed is:

1. In an environment comprising (i) a chip comprising a microchannel and (ii) an image sensor having a pixel array, wherein at least a portion of the microchannel is within a field of view of the pixel array, a nucleic acid analysis method comprising:
   introducing a sample of a solution comprising nucleic acid into the microchannel;
   forcing the sample to move though the microchannel;
   defining a first window of the pixel array;
   defining a second window of the pixel array, wherein the center of the second window is spaced apart from the center of the first window; and
   while the sample is moving through the microchannel, performing the steps of:
   (a) exposing the first window of the pixel array to light emitted from the sample at a time when the sample is within a field of view of first window and then selectively outputting first image data from the pixel array, wherein the step of selectively outputting the first image data from the pixel array comprises outputting data from only the first window of the pixel array; and
   (b) after performing step (a), exposing the second window of the pixel array to light emitted from the sample at a time when the sample is within a field of view of the second window and then selectively outputting second image data from the pixel array, wherein the step of selectively outputting the second image data from the pixel array comprises outputting data from only the second window of the pixel array.

2. The method of claim 1, wherein, when the step of exposing the first window of the pixel array to light emitted from the sample is performed, the center of the first window corresponds substantially to the center of the sample.

3. The method of claim 2, wherein, when the step of exposing the second window of the pixel array to light emitted from the sample is performed, the center of the second window corresponds substantially to the center of the sample.

4. The method of claim 1, wherein the size of the second window is less than the size of the first window.

5. The method of claim 4, wherein the step of defining the second window occurs after step (a).

6. The method of claim of claim 5, wherein the step of defining the second window comprises processing the first image data to determine whether the amount of light received at a pixel located at the edge of the first window exceeds or equals a predetermined threshold.

7. The method of claim 1, further comprising the step of receiving from a sensor a signal indicating that the sample has been detected by the sensor.

8. The method of claim 7, further comprising the step of receiving from a second sensor a second signal indicating that the sample has been detected by the second sensor, wherein the first sensor is positioned to detect when the sample enters the field of view of the image sensor and the second sensor is positioned to detect when the sample leaves the field of view of the image sensor.

9. The method of claim 1, wherein the step of defining the first window of the pixel array comprises determining the size of the window, wherein the determination is based, at least in part, on the length of the sample.

10. The method of claim 1, wherein the step of defining the first window of the pixel array comprises determining the size of the window, wherein the determination is based, at least in part, on the length of the sample, and the step of defining the second window of the pixel array comprises determining the location of the center of the second window, wherein the determination is based, at least in part, on a speed at which the sample moves through the microchannel.

11. A DNA analysis system, comprising:
a chip comprising a microchannel for receiving a sample of solution comprising nucleic acid and for providing a path for the sample to traverse;
an image sensor having a pixel array, wherein at least a portion of the microchannel is within a field of view of the pixel array; and
an image sensor controller configured to: (a) read only a first window of the pixel array at time when the sample is within a field of view of the first window, thereby producing first image data, and (b) read only a second window of the pixel array at time when the sample is within a field of view of the second window, wherein the center of the second window is spaced apart from the center of the first window, and wherein the image sensor controller is configured to determine a size for the first window, wherein the determination is based, at least in part, on the length of the sample, and the image sensor controller is configured to determine a location of the center of the second window, wherein the determination is based, at least in part, on a speed at which the sample moves through the channel.

12. A DNA analysis method comprising:
introducing a sample of a solution comprising nucleic acid into a microchannel;
causing the sample to move though the microchannel;
defining a first window of a pixel array of an image sensor;
defining a second window of the pixel array, wherein the center of the second window is spaced apart from the center of the first window;
while the sample is moving through the microchannel, performing the steps of:
(a) windowing the image sensor so that image data from the first window is output to a data buffer, wherein said image data comprises data from which the intensity of emissions from the sample can be determined using an image processor: and
(b) after performing step (a), windowing the image sensor so that image data from the second window is output to a data buffer, wherein said image data comprises data from which the intensity of emissions from the sample can be determined using an image processor;
wherein the step of defining the first window of the pixel array comprises determining the size of the window, wherein the determination is based, at least in part, on the length of the sample, and the step of defining the second window of the pixel array comprises determining the location of the center of the second window, wherein the determination is based, at least in part, on a speed at which the sample moves through the microchannel.

* * * * *